(12) United States Patent
Carr et al.

(10) Patent No.: US 6,682,522 B2
(45) Date of Patent: *Jan. 27, 2004

(54) VALVE FOR OSMOTIC DEVICES

(75) Inventors: John P. Carr, Sunnyvale, CA (US); James B. Eckenhoff, deceased, late of Los Altos, CA (US), by Bonnie Burdett Dennis, legal representative

(73) Assignee: Alza Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/310,742

(22) Filed: Dec. 4, 2002

(65) Prior Publication Data

US 2003/0093063 A1 May 15, 2003

Related U.S. Application Data

(63) Continuation of application No. 09/748,099, filed on Dec. 21, 2000, now Pat. No. 6,508,808
(60) Provisional application No. 60/171,305, filed on Dec. 21, 1999.

(51) Int. Cl.[7] .................................................. A61K 9/48
(52) U.S. Cl. ............................. 604/892.1; 604/890.1; 424/422; 424/457
(58) Field of Search ........................... 604/892.1, 890.1; 424/422, 457

(56) References Cited

U.S. PATENT DOCUMENTS

| | | |
|---|---|---|
| 2,168,437 A | 8/1939 | Buercklin |
| 3,732,865 A | 5/1973 | Higuchi et al. |
| 3,995,631 A | 12/1976 | Higuchi et al. |
| 3,995,632 A | 12/1976 | Nakano et al. |
| 4,111,202 A | 9/1978 | Theeuwes |
| 4,243,030 A | 1/1981 | Lynch et al. |
| 4,340,054 A | 7/1982 | Michaels |
| 4,350,271 A | 9/1982 | Eckenhoff |
| 4,373,527 A | 2/1983 | Fischell |
| 4,439,196 A | 3/1984 | Higuchi |
| 4,455,143 A | 6/1984 | Theeuwes et al. |
| 4,552,561 A | 11/1985 | Eckenhoff et al. |
| 4,639,244 A | 1/1987 | Rizk et al. |
| 4,865,845 A | 9/1989 | Eckenhoff et al. |
| 5,030,216 A | 7/1991 | Theeuwes et al. |
| 5,034,229 A | 7/1991 | Magruder et al. |
| 5,122,128 A | 6/1992 | Cardinal et al. |
| 5,221,278 A | 6/1993 | Linkwitz et al. |
| 5,223,265 A | 6/1993 | Wong |
| 5,279,608 A | 1/1994 | Cherif Cheikh |
| 5,308,348 A | 5/1994 | Balaban et al. |
| 5,312,389 A | 5/1994 | Theeuwes et al. |
| 5,312,390 A | 5/1994 | Wong |

(List continued on next page.)

FOREIGN PATENT DOCUMENTS

| | | |
|---|---|---|
| EP | 0 627 231 | 5/1994 |
| WO | 91/07160 | 5/1991 |
| WO | 94/09743 | 5/1994 |
| WO | 98/42317 | 10/1998 |

*Primary Examiner*—Henry C. Yuen
*Assistant Examiner*—Arnold Castro
(74) *Attorney, Agent, or Firm*—Burns, Doane, Swecker & Mathis, L.L.P.

(57) ABSTRACT

An osmotic delivery system for controlled delivery of a beneficial agent includes an implant capsule having a beneficial agent reservoir, an osmotic agent which expands on contact with fluid imbibed through a permeable membrane retained by the implant capsule, a delivery port, and a valve for opening and closing the delivery port. When the osmotic agent expands, a pressure is exerted against a separating member positioned between the beneficial agent reservoir and the osmotic agent. The separating member moves within the capsule, thereby forcing the valve to move a distance such that the beneficial agent can exit the reservoir through the delivery port.

39 Claims, 2 Drawing Sheets

U.S. PATENT DOCUMENTS

| | | |
|---|---|---|
| 5,318,558 A | 6/1994 | Linkwitz et al. |
| 5,456,679 A | 10/1995 | Balaban et al. |
| 5,498,255 A | 3/1996 | Wong |
| 5,639,477 A | 6/1997 | Maruyama et al. |
| 5,728,396 A | 3/1998 | Peery et al. |
| 5,795,591 A | 8/1998 | Lee et al. |
| 5,861,166 A | 1/1999 | Eckenhoff |
| 5,997,527 A | 12/1999 | Gumucio et al. |
| 6,217,906 B1 | 4/2001 | Gumucio et al. |
| 6,270,787 B1 * | 8/2001 | Ayer ................ 604/892.1 |
| 6,508,808 B1 * | 1/2003 | Carr et al. ........... 604/892.1 |
| 6,544,252 B1 * | 4/2003 | Theeuwes et al. ..... 604/892.1 |

* cited by examiner

VALVE FOR OSMOTIC DEVICES

This application is a continuation of U.S. patent application Ser. No. 09/748,099, filed on Dec. 21, 2000, now U.S. Pat. No. 6,508,808, which claims priority under 35 U.S.C. §§119 and/or 365 to U.S. Provisional Patent Application Serial No. 60/171,305, filed Dec. 21, 1999, both of which are incorporated herein by reference in their entirety.

BACKGROUND OF THE INVENTION

1. Field of the Invention

This invention relates to osmotic delivery devices for delivering beneficial agents, and more particularly, to osmotic delivery devices having an osmotic engine and a valve to prevent expulsion of the beneficial agents.

2. Description of the Related Art

Controlled delivery of beneficial agents, such as drugs, in the medical and veterinary fields has been accomplished by a variety of methods. One method for controlled prolonged delivery of beneficial agents involves the use of osmotic delivery systems. These systems can be implanted within a body of a human or animal to release beneficial agents in a controlled manner over a preselected time or administration period. In general, osmotic delivery systems operate by imbibing liquid from the outside environment and releasing corresponding amounts of the beneficial agent.

A known osmotic delivery system, commonly referred to as an "osmotic pump," generally includes some type of a capsule or enclosure having a semipermeable portion which selectively passes water into an interior of the capsule containing a water-attracting osmotic agent. In one known osmotic delivery system the walls of the capsule are substantially impermeable to items within and outside the capsule. A membrane plug is inserted into one end of the capsule and acts as the semipermeable portion allowing water to pass into the interior of the capsule. The difference in osmolarity between the water-attracting osmotic agent and the environment surrounding the capsule causes water to pass through the membrane plug into the capsule which in turn causes the beneficial agent within the capsule to be delivered through a delivery orifice. The water-attracting osmotic agent may be the beneficial agent delivered to the patient; however, in most cases a separate osmotic agent is used specifically for its ability to draw water into the capsule.

When a separate osmotic agent is used, the osmotic agent may be separated from the beneficial agent within the capsule by a movable dividing member or piston. The structure of the capsule is such that the capsule does not expand when the osmotic agent takes in water and expands. As the osmotic agent expands, it causes the piston to move and the beneficial agent to be discharged through the delivery orifice at the same rate as the liquid, which is typically water, enters the osmotic agent by osmosis. Osmotic delivery systems may be designed to deliver a beneficial agent at a controlled constant rate, a varying rate, or in a pulsatile manner.

In the known osmotic delivery systems, an osmotic tablet is generally used as the osmotic agent and is placed inside the capsule adjacent the piston. A membrane plug is placed in an opening in the capsule through which the tablet and piston were inserted. Known membrane plugs are typically cylindrical members which seal the interior of the capsule from the exterior environment, permitting only certain liquid molecules from the environment of use to permeate through the membrane plug into the interior of the capsule. The rate that the liquid permeates through the membrane plug controls the rate at which the osmotic agent expands and drives the beneficial agent from the delivery system through the delivery orifice. The rate of delivery of the beneficial agent from the osmotic delivery system may be controlled by varying the size of the beneficial agent delivery orifice, the osmotic material, a size and shape of the membrane plug, or the permeability coefficient of the membrane plug.

It is desirable to seal the beneficial agent delivery orifice of the delivery system to prevent incursion of materials into the delivery system before sufficient osmotic pressure exists to insure a flow of the beneficial agent through the orifice. Protecting the beneficial agent from the external environment is particularly important when the beneficial agent is a protein formulation or other agent which breaks down when in contact with certain environmental compositions.

In order to prevent contamination or early release of the beneficial agent, some delivery systems are provided with a plug in the orifice which is discharged upon movement of the piston by the fluid pressure within the system. Typically, such osmotic delivery systems use mechanical plugs, bio-eroding, or dissolving plugs.

With mechanical plugs, such plugs are chemically stable materials discharged from the delivery system on movement of a piston contained within the system. Premature release of the beneficial agent may occur when the delivery system is jarred, thereby loosening the mechanical plug from the system. Further, mechanical plugs expelled from the delivery device may not be acceptable with the patient when left in the patient's body at the implant site.

Bio-eroding or dissolving plugs also present drug delivery problems since such plugs allow the drug delivery orifice to open regardless of whether or not the osmotic agent can exert sufficient hydraulic pressure to insure flow of the beneficial agent.

Because of the above-identified problems associated with current osmotic delivery systems, it is desirable to prevent contamination of the beneficial agent and to prevent beneficial agent leakage by providing a delivery orifice valve which is not expelled into the patient's body.

SUMMARY OF THE INVENTION

The present invention relates to osmotic delivery systems having an osmotic engine and a valve to prevent contamination and/or expulsion of the beneficial agents.

In accordance with one aspect of the present invention, a delivery system for controlled delivery of a beneficial agent includes an implantable capsule having a delivery orifice, a separating member dividing the capsule into a beneficial agent reservoir and a driving reservoir, an osmotic engine in the driving reservoir, and a valve member that can move from a closed position to an open position. In the closed position, the valve member prevents the expulsion of beneficial agent from the beneficial agent reservoir through the delivery orifice. The implantable capsule can include an attachable cap having a vent. In operation, the osmotic engine imbibes fluid thereby causing the engine to swell. This swelling causes the osmotic engine to exert a pressure on the separating member whereby such pressure moves the separating member, the beneficial agent reservoir, and the valve member a distance such that the valve member moves to an open position, allowing passage of beneficial agent through the delivery orifice at a desired delivery rate.

In accordance with another aspect of the present invention, a method of preventing contamination from entering the osmotic delivery device before activation includes the steps of providing a delivery device capsule enclosing a first chamber which contains a beneficial agent and a valve member. The first chamber has an opening communicating with the external environment. Before activation of the delivery device, the valve member occludes the opening. This occlusion prevents the beneficial agent from leaving the device, as well as prevents the incursion of contaminants into the device.

In accordance with an additional aspect of the present invention, a method of controlling an initial release of a beneficial agent from an osmotic delivery device includes the steps of providing a delivery device capsule which encloses a first chamber containing the beneficial agent, a valve member, and a second chamber containing an osmotic agent. The first chamber has a beneficial agent delivery orifice communicating with the external environment. The valve member is initially in a closed position and blocks beneficial agent from passing through the beneficial agent delivery orifice. Upon implantation, the osmotic agent imbibes surrounding fluid to form an osmotic solute which expands and exerts a pressure on the first chamber. The osmotic imbibition of surrounding fluid builds pressure within the osmotic engine until sufficient force is exerted to move the first chamber and valve member, the valve member moving from the closed position to an open position. With the valve in the opened position, beneficial agent contained in the first chamber can pass through the beneficial agent delivery orifice to the external environment.

The present invention provides the advantage of a more controllable beneficial agent delivery rate by preventing expulsion of beneficial agent from the drug reservoir by using a valve to occlude the drug delivery orifice. The valve does not allow beneficial agent to pass through the delivery orifice until sufficient hydraulic pressure exists to displace the beneficial agent from the drug reservoir. Moreover, the present invention retains the valve within delivery device, whereby removing the implant from the patient after delivering the medication allows retrieval of both the valve and the implant device.

BRIEF DESCRIPTION OF THE FIGURES

The invention will now be described in greater detail with reference to the preferred embodiments illustrated in the accompanying drawings, in which like elements bear like reference numerals, and wherein.

DETAILED DESCRIPTION

The present invention relates to an osmotic delivery system for controlled delivery of a beneficial agent. FIGS. 1–4 illustrate two examples of osmotic delivery devices 10 according to the present invention.

Figure 1:
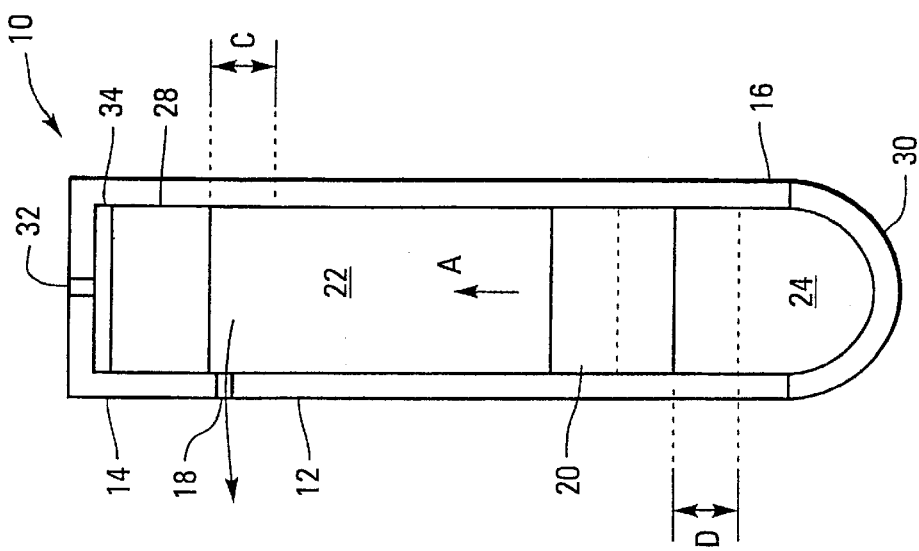
FIG. 1 is a side cross-sectional view of an osmotic delivery device according to the present invention.

The osmotic drug delivery device 10, as illustrated in FIG. 1, includes a movable valve 28, a first chamber 22 containing a beneficial agent, a separating member 20, and a second chamber 24 containing an osmotic engine or agent, all of which are enclosed within an elongated substantially cylindrical enclosure or capsule 12. The capsule 12 has a first end 14 and an open end 16. The first end 14 of the capsule 12 has one or more orifices or ports 18 for delivering a beneficial agent contained within a first chamber 22 of the osmotic delivery device 10 to an external environment. In most configurations, one delivery port 18 will suffice. However, two or more delivery ports 18 may be present without departing from the present invention.

The valve 28 occludes the delivery orifice 18 when the valve is in a closed position, preventing the beneficial agent in the first chamber 22 from leaving the delivery device 10 as well as preventing the incursion of foreign materials into the device. The dimensions of the valve 28 in terms of both diameter and length are selected such that the valve will not exit the delivery device 10 through the delivery orifice 18.

The separating member 20 also separates the first chamber 22 containing the beneficial agent from the second chamber 24 containing the osmotic agent. The separating member 20 and valve 28 are substantially cylindrical members which are configured to fit within the capsule 12 and are slidably movable along a longitudinal direction within the capsule. The separating member and valve 20, 28 preferably are formed of a resilient material which is impermeable to the compositions within the capsule 12, and at least a portion of the separating member 20 and the valve 28 forms a seal with the inner surface of said capsule 12.

In addition, the movable separating member and valve 20, 28 may be flexible members such as pistons, partitions, pads, flat sheets, spheroids, or rigid metal alloys, and may be made of any number of inert materials. Furthermore, the osmotic device 10 may function without the piston 20, having simply an interface between the osmotic agent and the beneficial agent.

A semipermeable membrane 30 couples with the capsule 12 at the open end 16 and encloses the second chamber 24 containing the osmotic agent. The osmotic agent may be, for example, a nonvolatile water soluble osmagent, an osmopolymer which swells on contact with water, or a mixture of the two. The elongated capsule 12 is formed of a material which is sufficiently rigid to withstand expansion of the osmotic agent contained within a second chamber 24 of the delivery device 10 without changing size or shape. The elongated capsule 12 is preferably substantially impermeable to fluids in the environment as well as to ingredients contained within the osmotic delivery device 10 such that the migration of such materials into or out of the device through the impermeable material of the capsule is so low as to have substantially no adverse impact on the function of the osmotic delivery device.

Figure 2:
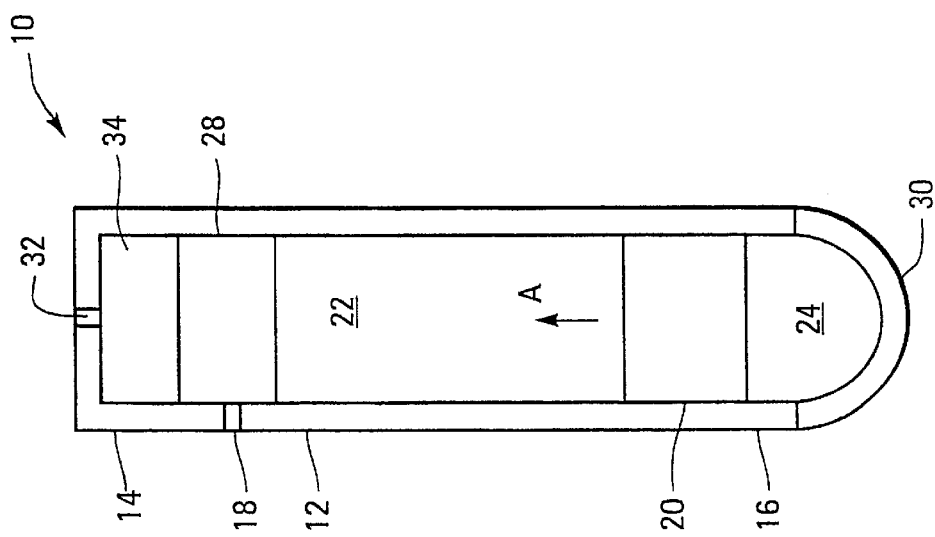
FIG. 2 is a side cross-sectional view of the osmotic delivery device of FIG. 1 delivering a beneficial agent through an orifice.

As shown in FIGS. 1 and 2, the osmotic delivery device 10 of one embodiment of the present invention includes a semipermeable membrane 30, which is coupled with the open end 16 of the capsule 12. In operation, after placing the osmotic agent within the second chamber 24 of the capsule, the semipermeable membrane 30 allows liquid to pass from an environment of use into the capsule 12 to cause the osmotic agent to swell. However, the material forming the semipermeable membrane 30 is largely impermeable to the materials within the capsule 12 and to other ingredients within the environment of use.

The swelling osmotic agent exerts a pressure on the separating member or piston 20 and forces said separating member to move a distance D in a direction of the arrow A. The separating member 20 applies a force to the beneficial agent in the first chamber 22, the beneficial agent transfers the force to the valve 28. Accordingly, this force causes the valve 28 to move a distance C from the close position to an open position. A clearance 34 between the valve 28 and the first end 14 decreases by the distance C. In the open position, the valve 28 allows the beneficial agent to pass through the delivery orifice 18 to the external environment of use.

The osmotic agent in conjunction with the separating member 20 drive the beneficial agent from the first chamber 22 and insures a flow of beneficial agent out of the delivery orifice 18. The valve 28 is retained within the delivery device 10 at the closed first end 14 of the capsule 12 and, as described above, the valve 28 has dimensions such that it will not leave the delivery device 10 through the delivery orifice 18. In a preferred embodiment, the capsule 12 has a vent 32 at the first end 14, allowing fluid to escape from the clearance 34 between the valve 28 and the capsule 12 when the valve 28 moves toward the first end 14.

Depending on the application, the clearance 34 between the valve 28 and the capsule 12 may be filled with a bio-compatible liquid or gas. The configuration of the osmotic delivery system and the material of the semipermeable membrane 30 control the delivery rate of a beneficial agent from the osmotic delivery system.

In assembling the osmotic delivery device 10 according to the embodiment of the present invention shown in FIGS. 1 and 2, the capsule 12 is prepared by forming at least one vent 32 at the first end 14 of the capsule. The vent 32 may be formed by mechanical drilling, laser drilling, molding, or any other known method. The delivery port 18 is an orifice formed by conventional techniques which are known in the art. Included among these methods are mechanical drilling, laser drilling, and molding. The dimensions of the delivery port 18 in terms of both diameter and length will vary with the type of beneficial agent, the rate at which the beneficial agent is to be delivered, and the environment into which it is to be delivered. The considerations involved in determining the optimum dimensions of the delivery port 18 for any particular capsule 12 or beneficial agent and the selection of the appropriate dimensions will be readily apparent to those skilled in the art.

Once the capsule 12 of FIGS. 1 and 2 has been prepared with the vent 32 and at least one delivery port 18, having a number, shape, and size to achieve a desired delivery rate of the beneficial agent, the valve 28 is inserted into the capsule 12 through the open end 16.

According to one embodiment of the present invention, the beneficial agent contained in the first chamber 22 of the capsule 12 is a flowable composition such as a liquid, suspension, or slurry, and is typically poured into the first chamber 22 of the capsule after the valve 28 has been inserted. The separating member 20 is inserted into the capsule 12 through the open end 16 and is positioned adjacent the beneficial agent.

Once the osmotic agent pellet(s) or tablet(s) have been formed, they are placed inside the pre-formed capsule in the second chamber 24 adjacent the separating member 20. Then the semipermeable membrane 30, according to one embodiment of the present invention, is placed into or over the open end 16 of the capsule 12 to close off and seal the open end of the osmotic delivery system.

Figure 4:
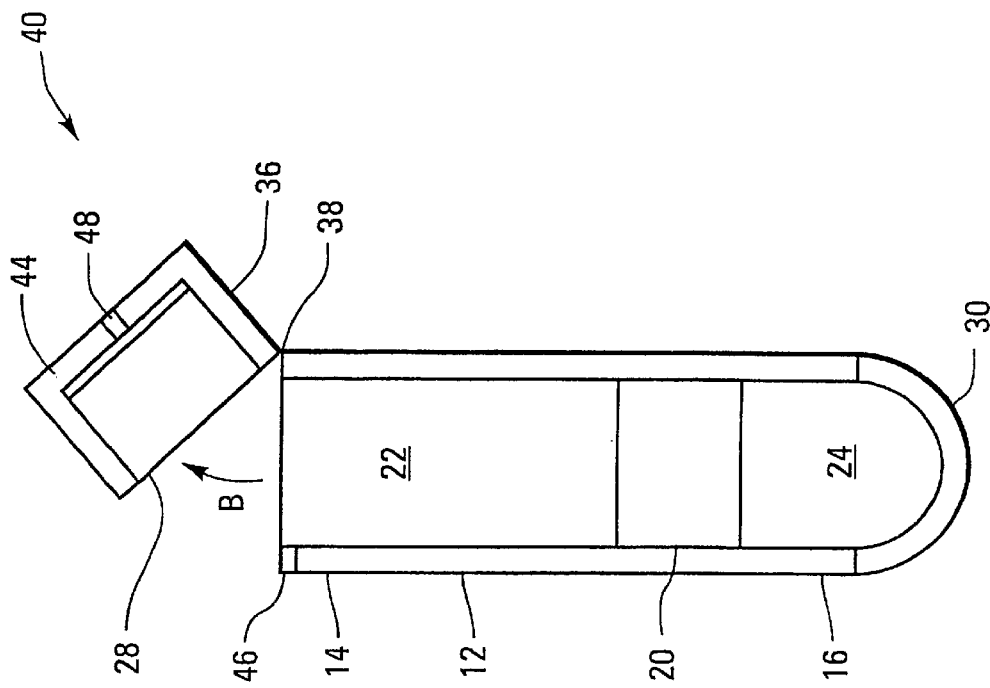
FIG. 4 is a side cross-sectional view of an osmotic delivery system having an alternative embodiment of a cap with the cap in opened position.
Figure 3:
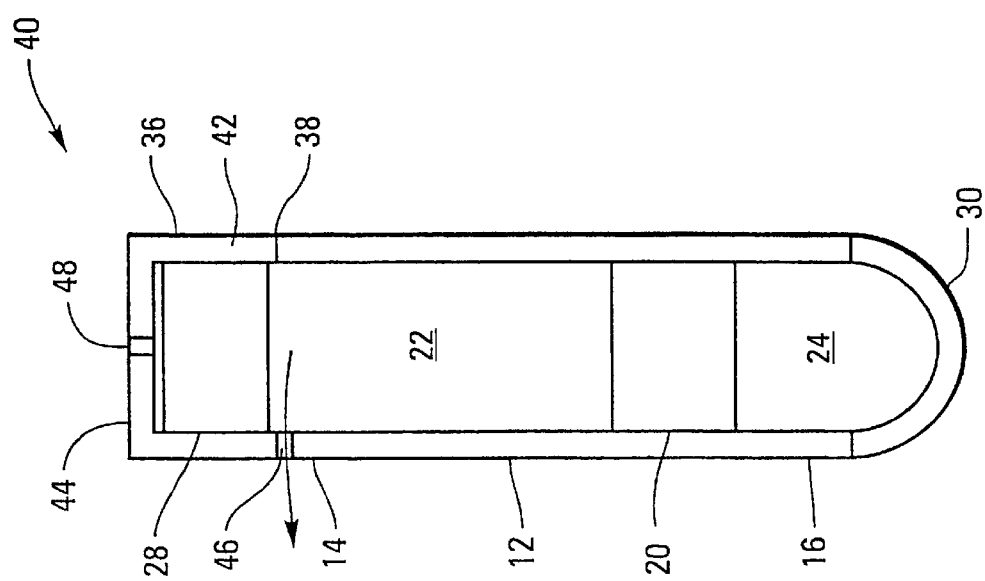
FIG. 3 is a side cross-sectional view of an osmotic delivery system having an alternative embodiment of a cap with the cap in closed position.

An alternative embodiment of the invention illustrated in FIGS. 3–4 includes a cap 36 having a hollow interior and a substantially constant thickness cylindrical side wall 42 and an end wall 44. The cap 36 forms the first end 50 of the capsule 12. In a preferred embodiment, the cap 36 affixes to the body of the capsule 12 by a snap fitting mechanism 38, such as a barbed stake. The cap 36 preferably has a vent 48 in the end wall 44 which after assembly allows the valve 28 to move in a direction towards the end wall 14. In a different embodiment, the cap 36 can be pivotally rotated about a hinge in a direction of the arrow B, as depicted in FIG. 4.

The first chamber 22 of the osmotic delivery device 40 has at least one opening 46 which communicates with the environment of use. As shown in FIG. 3, the opening 46 is formed in the body of the capsule 12 and is positioned adjacent the contacting surfaces of the cap. Alternatively, the opening 46 can be formed in the cap 36 and positioned adjacent the contacting surfaces of the body of the capsule 12. The semipermeable membrane 30 couples with the capsule 12 at the opened second end 52.

In assembling the osmotic delivery device 10 according to the embodiment of the present invention shown in FIGS. 3 and 4, the cap 36 is prepared by forming at least one vent 48 at the end wall 44. The vent 48 may be formed by mechanical drilling, laser drilling, molding, or any other known method.

The capsule 12 is prepared having an opened first end 50 and an opened second end 52. The delivery port 46 is an orifice positioned at the edge of the cap 36 adjacent the capsule 12, or the delivery port 46 is positioned at the edge of the capsule 12 adjacent the cap 36. The delivery port 18 is formed by conventional techniques which are known in the art. Included among these methods are laser drilling, mechanical drilling, grooving the edge of the capsule or cap, and molding.

The separating member 20 is inserted into the capsule 12 through the first or second end 50, 52. Once the osmotic agent pellet(s) or tablet(s) have been formed, they are placed inside the capsule 12 in the second chamber 24, adjacent the separating member 20. The semipermeable membrane 30 is placed into or over the second end 52 to Lose off and seal that end.

Beneficial agent is added into the first chamber 22 of the capsule 12 through the first end 50, and the valve 28 is inserted adjacent the beneficial agent in a closed position. As discussed, the valve 28 in a closed position prevents the beneficial agent from leaving the delivery device 10 and prevents incursion of foreign materials into the device. Then the cap 36 is placed at the first end 50 of the capsule to close off and seal that open end of the osmotic delivery system 10. The cap 36 may be secured to the capsule 12 by press fitting, snap fitting, threading, adhesive, welding, staking, or the like.

In general, materials suitable for use in the movable separating member 20 and the valve 28 are elastomeric materials including non-reactive polymers, as well as elastomers in general, such as polyurethanes and polyamides, chlorinated rubbers, styrene-butadiene rubbers, and chloroprene rubbers. The polymers include acrylonitrile polymers such as acrylonitrile-butadiene-styrene terpolymer, and the like, halogenated polymers such as polytetraflouroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like.

Semipermeable compositions suitable for the semipermeable membrane 30 are well known in the art, examples of which are disclosed in U.S. Pat. No. 4,874,388, the entire disclosure of which is incorporated herein by reference. Such possible semipermeable materials from which the membrane 30 can be made include, but are not limited to, for example, Hytrel polyester elastomers (DuPont), cellulose esters, cellulose ethers, and cellulose ester-ethers, water flux enhanced ethylene-vinyl acetate copolymers, semipermeable membranes made by blending a rigid polymer with water-soluble low molecular weight compounds, and other semipermeable materials well known in the art. The above cellulosic polymers have a degree of substitution, D.S., on the anhydroglucose unit, from greater than 0 up to 3 inclusive. By "degree of substitution" or "D.S." is meant the average number of hydroxyl groups originally present on the anhydroglucose unit comprising the cellulose polymer that are replaced by a substituting group. Representative materials include, but are not limited to, one selected from the group consisting of cellulose acylate, cellulose diacylate, cellulose triacylate, cellulose acetate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21%; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53%, and a hydroxyl content of 0.5% to 4.7%; cellulose acetate butyrate having a D.S. of 1.8, an acetyl content of 4% average weight percent, and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like.

Other materials for the membrane 30 are polyurethane, polyetherblockamide (PEBAX, commercially available from ELF ATOCHEM, Inc.), and injection-moldable thermoplastic polymers with some hydrophilicity such as ethylene vinyl alcohol (EVA). In general, the membrane 30 is made from semipermeable materials having a water uptake ranging from 1% to 80% but preferably less than 50%. The composition of the semipermeable membrane 30 is permeable to the passage of external liquids such as water and biological liquids, and it is substantially impermeable to the passage of beneficial agents, osmopolymers, osmagents, and the like.

Materials which may be used for the capsule 12 and the cap 36 must be sufficiently strong to ensure that the capsule will not leak, crack, break, or distort under stresses to which it is subjected during implantation or under stresses due to the pressures generated during operation. The capsule 12 may be formed of chemically inert and biocompatible, natural or synthetic materials which are known in the art. The capsule material is preferably a nonbioerodible material which remains in the patient after use, such as titanium or a titanium alloy, and is largely impermeable to materials within and outside the capsule. However, the material of the capsule 12 may alternatively be a bioerodible material which bioerodes in the environment after dispensing of the beneficial agent. Generally, preferred materials for the capsule 12 are those acceptable for animal and human implants.

In general, typical materials of construction suitable for the capsule 12 according to the present invention include non-reactive polymers or biocompatible metals or alloys. Metallic materials useful for the capsule 12 include stainless steel, titanium, platinum, tantalum, gold, and their alloys, as well as gold-plated ferrous alloys, platinum-plated ferrous alloys, cobalt-chromium alloys and titanium nitride coated stainless steel.

The capsule 12 may be formed from any of the wall-forming materials disclosed above by the use of a mold, with the materials applied either over the mold or inside the mold, depending on the mold configuration. Any of the wide variety of techniques known in the pharmaceutical industry may be used to form the capsule 12.

The osmotic agent is a liquid-attracting agent used to drive the flow of the beneficial agent. The osmotic agent may be an osmagent, an osmopolymer, or a mixture of the two. Species which fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic, and examples of osmopolymers are well known in the art. Examples include: poly(hydroxyalkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross linked with glyoxal, formaldehyde, or glutaraldehyde and having a degree of polymerization of 200 to 30,000, a mixture of methyl cellulose, cross linked agar and carboxymethylcellulose, a mixture of hydroxypropl methycellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyuria gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross linked indene-maleic anhydride polymers, Good-Rite polyacrylic acids having molecular weights of 80,000 to 200,000, Polyox Polyethylene oxide polymers having molecular weights of 100,000 to 5,000,000, starch graft copolymers, and Aqua-Keeps acrylate polymer polysaccharides.

The osmotic agent may be a solid osmotic tablet or a fluid osmotic agent. The osmotic tablet may be formed in many different conceivable shapes, textures, densities, and consistencies and still be within the confines of the present invention. The osmotic agent may be manufactured by a variety of techniques, many of which are known in the art. In one such technique, the osmotically active agent is prepared as solid or semi-solid formulation and pressed into pellets or tablets whose dimensions correspond to slightly less than the internal dimensions of the respective chambers which they will occupy in the capsule interior. Depending on the nature of the materials used, the agent and other solid ingredients which may be included may be processed prior to the formation of the pellets by such procedures as ballmilling, calendaring, stirring, or rollmilling to achieve a fine particle size and hence fairly uniform mixtures of each.

The present invention applies to the administration of beneficial agents in general, which include any physiologically or pharmacologically active substance. Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention include, but are not limited to prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-αhydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mando, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, prolactin, somatostatin, lypressin, pancreozymin, luteinizing hormone, LHRH, LHRH agonists and antagonists, leuprolide, interferons, interleukins, growth hormones such as human growth hormone, bovine growth hormone and porcine growth hormone, fertility inhibitors such as the prostaglandins, fertility promoters, growth factors, coagultion factors, human pancreas hormone releasing factor, analogs and derivatives of these compounds, and pharmaceutically acceptable salts of these compounds, or their analogs or derivatives.

On the molecular level, the various forms of the beneficial agent may include uncharged molecules, molecular complexes, and pharmaceutically acceptable acid addition and base addition salts such as hydrochlorides, hydrobromides, acetate, sulfate, laurylate, oleate, and salicylate. For acidic compounds, salts of metals, amines or organic cations may be used. Derivatives such as esters, ethers and amides can also be used. A beneficial agent can be used alone or mixed with other agents. The beneficial agent may optionally include pharmaceutically acceptable carriers and/or additional ingredients such as antioxidants, stabilizing agents, permeation enhances, and the like.

Animals to whom beneficial agents may be administered using systems of this invention include humans and other animals. The invention is of particular interest for application to humans and household, sport, and farm animals, particularly mammals. For the administration of beneficial agents to animals, the devices of the present invention may be implanted subcutaneously or intraperitoneally wherein aqueous body fluids are available to activate the osmotic agent. Devices of the invention may also be administered to the rumen of ruminant animals, in which embodiment the devices may further comprise a density element for maintaining the device in the rumen for extended periods of time of up to 120 days or longer. Density elements are well known in the art of drug delivery devices.

The delivery devices of this invention are also useful in environments outside of physiological or aqueous environments. For example, the delivery devices may be used in intravenous systems (attached to an IV pump or bag or to an IV bottle, for example) for delivering beneficial agents to an animal, primarily to humans. They may also be utilized in blood oxygenators, kidney dialysis and electrophoresis, for example. Additionally, delivery devices of the present invention may be used in the biotechnology area, such as to deliver nutrients or growth regulating compounds to cell cultures. In such instances, activating mechanisms such as mechanical mechanisms are particularly useful. The beneficial agent may be any of the agents which are known to be delivered to the body of a human or an animal such as medicaments, vitamins, nutrients, or the like. The beneficial agent may also be an agent which is delivered to other types of aqueous environments such as pools, tanks, reservoirs, and the like. Included among the types of agents which meet this description are biocides, sterilization agents, nutrients, vitamins, food supplements, sex sterilants, fertility inhibitors and fertility promoters.

While the invention has been described in detail with reference to preferred embodiments thereof, it will be apparent to one skilled in the art that various changes can be made, and equivalents employed without departing from the invention.

What is claimed is:

1. An osmotic delivery device for delivery of a beneficial agent, comprising:
   an implantable capsule having a beneficial agent delivery orifice, the beneficial agent delivery orifice positioned between a first end and a second end of the implantable capsule;
   a separating member positioned within the capsule between the first and second ends, the separating member dividing said capsule into a beneficial agent reservoir and a driving reservoir;
   an osmotic agent positioned in the driving reservoir; and
   a valve member positioned with an interior of the capsule between the first end and the beneficial agent reservoir such that the valve member opens and closes the beneficial agent delivery orifice.

2. The osmotic delivery device of claim 1, wherein the valve member is positioned within the capsule such that it separates the beneficial agent reservoir from a separate clearance area within the capsule.

3. The osmotic delivery device of claim 1, wherein the implantable capsule has an inner surface and an outer surface, and the valve member is positioned adjacent to the inner surface.

4. The osmotic delivery device of claim 1, further comprising a permeable membrane retained by the capsule and separating the osmotic agent from a surrounding fluid, wherein in operation, the osmotic agent imbibes the surrounding fluid through the permeable membrane, said osmotic agent forming an osmotic solute which exerts a pressure on the separating member and forces said separating member to move within the capsule, thereby moving the valve member to allow delivery of the beneficial agent through the beneficial agent delivery orifice.

5. The osmotic delivery device of claim 4, wherein the permeable membrane retained by the capsule controls a rate at which the surrounding fluid is imbibed into the osmotic agent, the rate at which said surrounding fluid is imbibed into the osmotic agent controlling a delivery rate of the beneficial agent.

6. The osmotic delivery device of claim 1, wherein the first end of the capsule includes a vent which allows fluid trapped between the valve member and the first end to escape from the capsule as the valve member moves.

7. The osmotic delivery device of claim 1, wherein the capsule provides a clearance between the valve member and the first end, wherein the clearance can receive at least a portion of said valve member in an open position.

8. The osmotic delivery device of claim 1, wherein at least a portion of the separating member forms a seal with an inner surface of the capsule.

9. The osmotic delivery device of claim 1, wherein at least a portion of the valve member has a length greater than a diameter of the beneficial agent delivery orifice.

10. The osmotic delivery device of claim 1, further comprising a cap forming the first end of the capsule, the cap capable of receiving at least a portion of said valve member.

11. The osmotic delivery device of claim 10, wherein the cap is attachable to a body of the capsule with a snap fitting mechanism.

12. The osmotic delivery device of claim 10, wherein the cap is hingedly attached to a body of the capsule.

13. The osmotic delivery device of claim 1, wherein the separating member is movable within the capsule.

14. An osmotic delivery device, comprising:
   an implantable capsule having first and second ends, the capsule containing an osmotic agent and a beneficial agent; and
   a beneficial agent delivery orifice located adjacent to a valve member, wherein the valve member is positioned within an interior of the capsule and movable from a closed position to an open position in response to fluid pressure created by the osmotic agent, in the closed position the valve member blocks fluid flow through the beneficial agent delivery orifice, and in the open position allows passage of fluid through the beneficial agent delivery orifice.

15. The osmotic delivery device of claim 14, further comprising a cap forming the first end of the capsule.

16. The osmotic delivery device of claim 15, wherein the beneficial agent delivery orifice is positioned adjacent the cap.

17. The osmotic delivery device of claim 14, further comprising:
   a movable separating member between the osmotic agent and the beneficial agent; and
   a permeable membrane retained by the capsule and separating the osmotic agent from a surrounding fluid, wherein in operation, the osmotic agent imbibes the surrounding fluid through the permeable membrane, said osmotic agent forming an osmotic solute which exerts a pressure on the separating member and forces said separating member to move within the capsule, thereby moving the valve member to allow delivery of the beneficial agent through the beneficial agent delivery orifice.

18. A method of preventing contamination from entering an osmotic delivery device before activation, comprising the steps of:
   providing a delivery device capsule which encloses a first chamber containing a beneficial agent, the first chamber having a beneficial agent delivery orifice communicating with an external environment, and a valve member movable within the capsule; and
   positioning the valve member in the delivery device capsule, such that the valve member occludes the beneficial agent delivery orifice.

19. The method of claim 18, further comprising the step of providing an osmotic agent which imbibes a surrounding fluid into the osmotic agent to form an osmotic solute which expands and exerts a pressure on the beneficial agent and the valve member, wherein the pressure moves the valve member to a position wherein the valve member does not occlude the beneficial agent delivery orifice.

20. The method of claim 19, further comprising the step of providing a movable separating member between the osmotic agent and the beneficial agent such that the valve member in the opened position allows the separating member to drive the beneficial agent from the first chamber, thereby insuring a flow of beneficial agent through the beneficial agent delivery orifice and preventing contamination from entering the delivery device.

21. A method of controlling an initial release of a beneficial agent from an osmotic delivery device, comprising the steps of:
   providing a delivery device capsule which encloses a first chamber containing a beneficial agent, a valve member, and a second chamber containing an osmotic agent, wherein the first chamber has a beneficial agent delivery orifice;
   positioning the valve member in the delivery device capsule, wherein before activation the valve member occludes the delivery orifice preventing passage of the beneficial agent contained in the first chamber through the beneficial agent delivery orifice; and imbibing a surrounding fluid into the osmotic agent to form an osmotic solute which expands and exerts a pressure on the beneficial agent and the valve member, wherein the pressure moves the valve member to a position allowing the beneficial agent contained in the first chamber to pass through the beneficial agent delivery orifice.

22. An osmotic delivery device for delivery of a beneficial agent, comprising:
   an implantable capsule having a hollow interior and substantially cylindrical side wall and a first end wall and a second end wall, the implantable capsule including:
      a cap forming the first end wall of the implantable capsule; and
      a capsule body forming the second end wall of the capsule;
   a beneficial agent delivery orifice positioned in the cylindrical sidewall between the first and second ends;
   a separating member positioned within the capsule between the first and second ends, the separating member dividing said capsule into a beneficial agent reservoir and a driving reservoir;
   an osmotic agent positioned in the driving reservoir; and
   a valve member positioned within the capsule between the first end and the beneficial agent reservoir such that the valve member occludes the beneficial agent delivery orifice in a first position and allows delivery of a beneficial agent in a second position.

23. The osmotic delivery device of claim 22, wherein the cap affixes to the body of the capsule by a snap fitting mechanism.

24. The osmotic delivery device of claim 23, wherein the snap fitting mechanism is a barbed stake.

25. The osmotic delivery device of claim 22, wherein the cap has a vent in the end wall which after assembly allows the valve to move in a direction towards the end wall.

26. The osmotic delivery device of claim 22, wherein the cap affixes to the capsule body by a hinge.

27. The osmotic delivery device of claim 22, wherein the capsule has at least one opening which communicates with the environment of use.

28. The osmotic delivery device of claim 27, wherein the opening is formed in the capsule body and is positioned adjacent a capsule contacting surface of the cap.

29. The osmotic delivery device of claim 27, wherein the opening is formed in the cap and positioned adjacent a cap contacting surface of the capsule body.

30. The osmotic delivery device of claim 22, wherein the semi-permeable membrane couples with the capsule at the opened second end.

31. The osmotic delivery device of claim 22, wherein the delivery orifice is positioned at an edge of the cap adjacent the capsule.

32. The osmotic delivery device of claim 22, wherein the delivery orifice is positioned at an edge of the capsule adjacent the cap.

33. The osmotic delivery device of claim 22, wherein said valve member is movable in a longitudinal direction within said capsule.

34. The osmotic delivery device of claim 22, further comprising a permeable membrane retained by the capsule and separating the osmotic agent from a surrounding fluid, wherein in operation, the osmotic agent imbibes the surrounding fluid through the permeable membrane, said osmotic agent forming an osmotic solute which exerts a pressure on the separating member and forces said separating member to move within the capsule, thereby moving the valve member to allow delivery of the beneficial agent through the beneficial agent delivery orifice.

35. The osmotic delivery device of claim 34, wherein the permeable membrane retained by the capsule controls a rate at which the surrounding fluid is imbibed into the osmotic agent, the rate at which said surrounding fluid is imbibed into the osmotic agent controlling a delivery rate of the beneficial agent.

36. The osmotic delivery device of claim 22, wherein a vent allows fluid trapped between the valve member and the cap to escape from the capsule as the valve member moves.

37. The osmotic delivery device of claim 22, wherein the capsule provides a clearance between the valve member and the first end, wherein the clearance can receive at least a portion of said valve member in an open position.

38. The osmotic delivery device of claim 22, wherein at least a portion of the separating member forms a seal with an inner surface of the capsule.

39. The osmotic delivery device of claim 22, wherein at least a portion of the valve member has a length greater than a diameter of the beneficial agent delivery orifice.

* * * * *